(12) United States Patent
Liu

(10) Patent No.: US 9,950,195 B2
(45) Date of Patent: Apr. 24, 2018

(54) RADIOTHERAPEUTIC SYSTEM AND DRIVING CONTROL METHOD THEREOF

(71) Applicant: Xi'an Cyber Medical Technology Co., Ltd., Xi'an (CN)

(72) Inventor: Haifeng Liu, Xi'an (CN)

(73) Assignee: XI'AN CYBER MEDICAL TECHNOLOGY CO., LTD., Xi'An (CN)

( * ) Notice: Subject to any disclaimer, the term of this patent is extended or adjusted under 35 U.S.C. 154(b) by 0 days.

(21) Appl. No.: 15/351,497

(22) Filed: Nov. 15, 2016

(65) Prior Publication Data

US 2017/0065834 A1 Mar. 9, 2017

Related U.S. Application Data

(63) Continuation-in-part of application No. 14/437,333, filed on Apr. 21, 2015, now Pat. No. 9,526,919.

(51) Int. Cl.
| | |
|---|---|
| *A61N 5/10* | (2006.01) |
| *G21K 1/04* | (2006.01) |
| *A61B 6/02* | (2006.01) |
| *A61B 6/00* | (2006.01) |

(52) U.S. Cl.
CPC .......... *A61N 5/1082* (2013.01); *A61B 6/022* (2013.01); *A61B 6/486* (2013.01); *A61N 5/1047* (2013.01); *A61N 5/1084* (2013.01); *A61N 5/1045* (2013.01); *A61N 5/1049* (2013.01); *A61N 5/1064* (2013.01); *A61N 2005/1061* (2013.01)

(58) Field of Classification Search
CPC ...... A61N 5/1084; A61N 5/1081; A61N 5/01; A61N 5/10; A61N 5/1065; A61N 5/1077; A61N 5/1082; G21K 1/046
USPC .............. 250/341.7, 494.1, 505.1; 600/427; 378/65, 207, 63, 64
See application file for complete search history.

(56) References Cited

U.S. PATENT DOCUMENTS

| | | | | |
|---|---|---|---|---|
| 5,537,452 | A * | 7/1996 | Shepherd | A61N 5/103 378/148 |
| 7,831,013 | B2 * | 11/2010 | Star-Lack | A61B 6/025 378/23 |
| 8,139,714 | B1 * | 3/2012 | Sahadevan | A61N 5/025 378/63 |
| 8,173,983 | B1 * | 5/2012 | Sahadevan | A61N 5/1084 250/341.7 |
| 8,254,521 | B2 * | 8/2012 | Brooks | A61B 6/502 378/37 |
| 8,300,766 | B2 * | 10/2012 | Handa | A61B 6/022 378/207 |
| 8,637,841 | B2 * | 1/2014 | Prince | G21K 1/046 250/492.1 |
| 8,682,414 | B2 * | 3/2014 | Nishimoto | A61N 5/103 378/62 |
| 8,712,011 | B2 * | 4/2014 | Robar | A61N 5/1049 378/62 |

(Continued)

*Primary Examiner* — David A Vanore
(74) *Attorney, Agent, or Firm* — Hemisphere Law, PLLC; Zhigang Ma

(57) ABSTRACT

The present disclosure discloses a radiotherapeutic system. The radiotherapeutic system comprises a gantry and at least two radiotherapeutic heads disposed to the gantry. The at least two radiotherapeutic heads comprises at least one focused radiotherapeutic head with multi-source and at least one conformal and intensity-modulated radiotherapeutic head.

20 Claims, 6 Drawing Sheets

(56) References Cited

U.S. PATENT DOCUMENTS

| | | | |
|---|---|---|---|
| 9,149,654 B2* | 10/2015 | Handa | A61N 5/1049 |
| 9,149,656 B2* | 10/2015 | Tanabe | A61N 5/1067 |
| 9,155,910 B1* | 10/2015 | Sahadevan | A61N 5/1077 |
| 9,283,403 B2* | 3/2016 | Mazin | A61B 6/037 |
| 9,581,762 B2* | 2/2017 | Wertsberger | G01J 3/0256 |
| 9,694,210 B2* | 7/2017 | Liu | A61N 5/1082 |
| 2012/0076269 A1* | 3/2012 | Roberts | A61N 5/1049 |
| | | | 378/65 |
| 2012/0307973 A1* | 12/2012 | Dirauf | A61B 6/032 |
| | | | 378/62 |
| 2014/0321615 A1* | 10/2014 | Carlsson | A61N 5/1049 |
| | | | 378/62 |
| 2015/0251022 A1* | 9/2015 | Liu | A61N 5/1081 |
| | | | 600/1 |
| 2016/0038768 A1* | 2/2016 | Liu | A61N 5/1082 |
| | | | 378/62 |
| 2016/0220848 A1* | 8/2016 | Adler, Jr. | A61N 5/1082 |
| 2017/0028221 A1* | 2/2017 | Kontaxis | A61N 5/1038 |
| 2017/0065833 A1* | 3/2017 | Liu | A61N 5/1082 |

* cited by examiner

RADIOTHERAPEUTIC SYSTEM AND DRIVING CONTROL METHOD THEREOF

CROSS-REFERENCE TO RELATED APPLICATION

This application is a continuation-in-part of U.S. application Ser. No. 14/437,333, filed on Apr. 21, 2015, which is hereby incorporated by reference herein.

TECHNICAL FIELD

The disclosure relates to the technical field of medical equipment, and more particularly to a radiotherapeutic system and driving control method thereof.

BACKGROUND

Radiation therapy is a common treatment for treating a tumor. There are generally two kinds of radiotherapy for the treatment, one for stereotactic focused radiation therapy with multi-source and another for intensity-modulated radiation therapy (IMRT). Regarding the stereotactic multi-source focused radiation therapy method, a plurality of radiation beams emitting from one multi-source focused therapeutic head, which is installed on a treatment equipment, are focused to one focal point (namely, the target region), so that high-dose irradiation is performed on the tumor which is in the target region. This multi-source focused radiation therapy method may be adopted to perform high-dose irradiation for tumor tissues while reducing radiation damage for surrounding tissues. This multi-source focused radiation therapy method, with a precise therapeutic property, has a very good therapeutic effect for intracranial tumors or head and neck tumors. However, for a body tumor that has a complicated shape or that is large, the foregoing multi-source focused radiation therapy method has its limits, and the conformal intensity modulated radiation therapy method would be required. The so-called conformal intensity modulated radiotherapy means that the therapeutic equipment comprises a conformal therapeutic head, generally an accelerator, and a multi-leaf collimator which is used to form a beam-passable region which is similar to the tumor shape. As such, the area of the target region or at least part of the target region can be irradiated by the radiation beams, to achieve the purpose of conformal treatment.

Currently, there is no radiation therapy device that can integrate the stereotactic multi-source focused radiation therapy method with the conformal and intensity-modulated radiation therapy method. In other words, a single current radiation therapy device cannot implement both accurate multi-source focused therapy and conformal therapy. Therefore, it is impossible to provide different treatment options in the same device for different or same tumors.

SUMMARY

The present disclosure provides a radiotherapeutic system and driving control method thereof. The radiotherapeutic system includes a focused radiotherapeutic head with multi-source and a conformal and intensity-modulated radiotherapeutic head. The radiotherapeutic system can implement a synergistic therapy process with different therapeutic heads on a single radiotherapy equipment, improving the therapy efficiency and therapy effect.

On one hand, the present disclosure provides a radiotherapeutic system comprising a gantry and at least two radiotherapeutic heads disposed to the gantry, and the at least two radiotherapeutic heads comprise at least one focused radiotherapeutic head with multi-source and at least one conformal and intensity-modulated radiotherapeutic head.

On the other hand, the present disclosure provides a driving control method for the radiotherapeutic system. The radiotherapeutic system comprises a controller and a rotation driving means. The driving control method comprises the step of: sending a first driving control signal to the rotation driving means by the controller, and receiving the first driving control signal and drives the gantry to continuously or reciprocally rotate around the axis of the gantry by 360 degrees by rotation driving means.

The present embodiment provides a radiotherapeutic system and driving control method thereof, the radiotherapeutic system comprises a gantry and at least two radiotherapeutic heads disposed to the gantry, and the at least two radiotherapeutic heads comprise at least one focused radiotherapeutic head with multi-source and at least one conformal and intensity-modulated radiotherapeutic head. The conformal and intensity-modulated radiotherapeutic head can perform conformal therapy to large area of a tumor, and the focused radiotherapeutic head can perform a dose enhancement therapy to part of the tumor, thereby achieving a synergistic therapy process with a plurality of therapeutic heads and completing the conformal and intensity modulation therapy, improving the accuracy and efficiency of treatment.

DETAILED DESCRIPTION

For making the purpose, the technical proposal and advantages of embodiments of the disclosure more clear, the technical proposal of the embodiments of this disclosure may be described clearly and fully using the figures included. Clearly, the described embodiments are only parts of the embodiments of this disclosure and not all of the embodiments. Based on the embodiments of this disclosure, all other embodiments obtained without contributing any creative effect by those skilled in the art are within the scope of protection of this disclosure.

Figure 1:
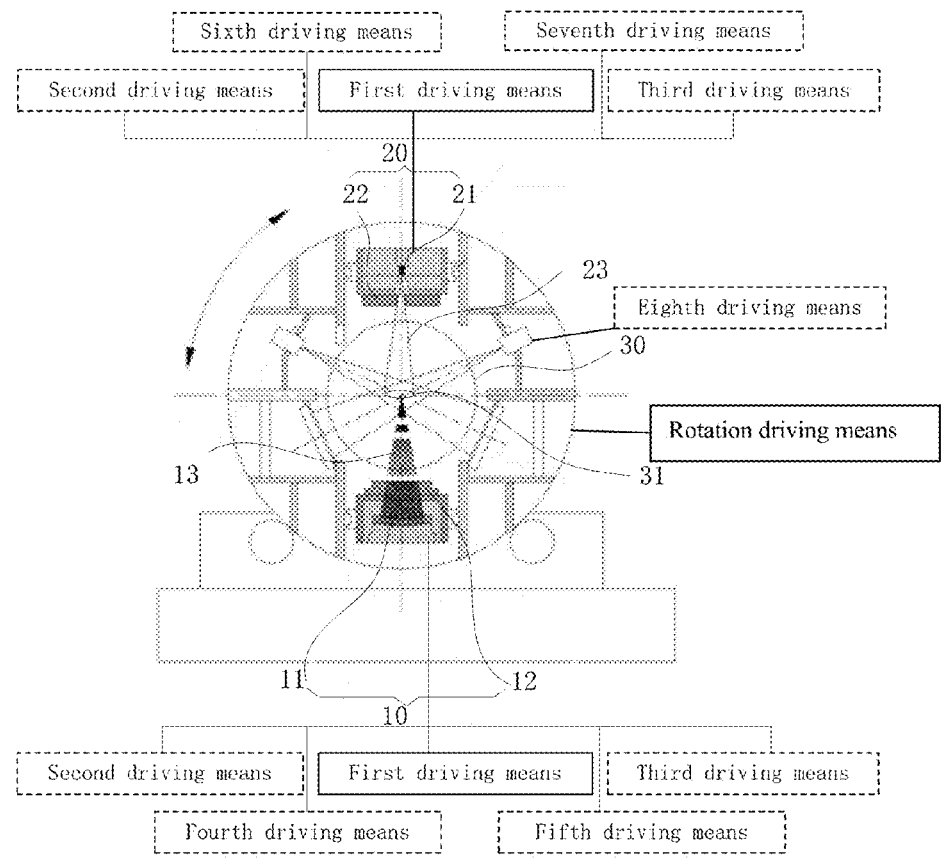
FIG. 1 is a schematic view of a radiotherapeutic system according to an embodiment of the present disclosure.
Figure 2:
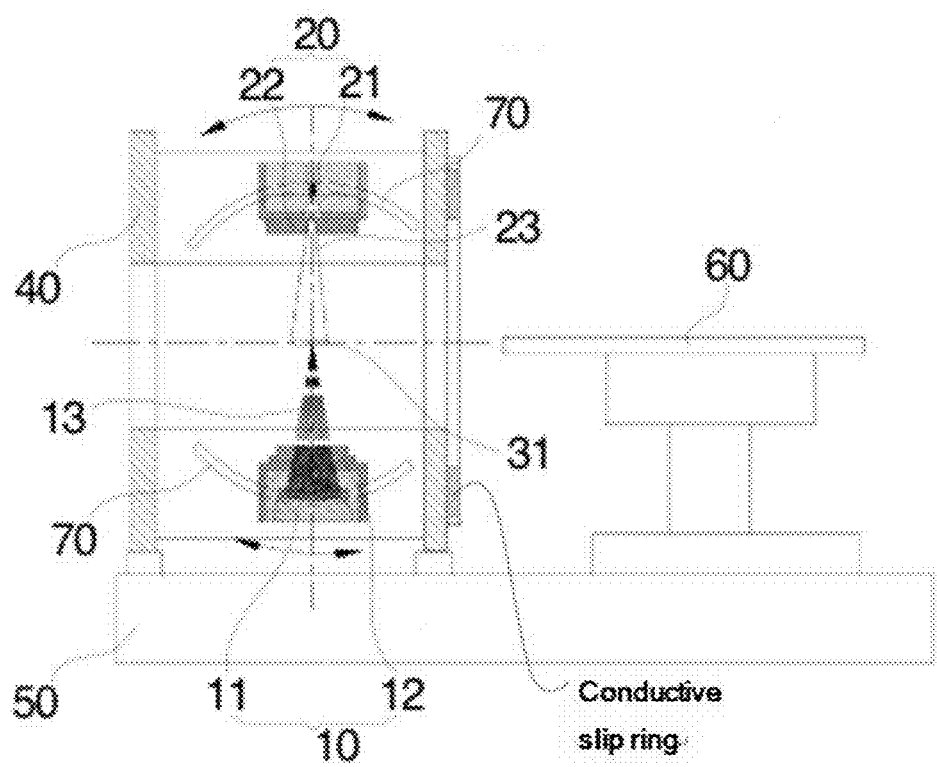
FIG. 2 is a side view of the radiotherapeutic system of FIG. 1.

As shown in FIGS. 1 and 2, a radiotherapeutic system according to an embodiment of the present disclosure, includes a gantry and at least two therapeutic heads provided on the gantry. The at least two therapeutic heads include at least one focused therapeutic head and at least one conformal therapeutic head.

Wherein the at least two therapeutic heads including at least one focused therapeutic head and at least one conformal therapeutic head may include one or two or more for each type of therapeutic head. For example, the radiotherapeutic system may include one focused therapeutic head and one conformal therapeutic head, or the radiation treatment system may include two focused therapeutic heads and a conformal therapeutic head, or the radiotherapeutic system may include two focused therapeutic heads and two conformal therapeutic heads. As shown in FIGS. 1 and 2, in this disclosure, illustratively, the radiotherapeutic system includes a focused therapeutic head 10 and a conformal therapeutic head 20, and the focused therapeutic head 10 is disposed opposite the conformal therapeutic head 20.

A focused therapeutic head generally refers to a therapeutic head comprising a plurality of radioactive sources, all radioactive sources are focused on one focal point. The focal point can move to different regions of the tumor for performing treatment therein. A conformal therapeutic head generally refers to a therapeutic head comprising one radioactive source emitting a scattered cone beam, and a collimator or a multi-leaf collimator configured therein forming a beam-passable region similar to the shape of the tumor. The cone beam is irradiated to the tumor through the beam-passable region, thereby realizing the radiation therapy of the tumor.

Illustratively, referring FIGS. 1 and 2, the focused therapeutic head 10 includes a plurality of first radioactive sources 11 each being capable of emitting a first radiation beam 13. The field diameter of the first radiation beam 13 can be adjusted through a collimator 12. The plurality of first radiation beams 13 are focused on a focal point that is irradiated on a partial region of the tumor 31 of the human body 30. The conformal therapeutic head 20 includes a second radioactive source 21 that emits a scattered cone beam 23. A multi-leaf collimator 22 forms a beam-passable region which is similar to the tumor shape. As such, the tumor 31 can be irradiated by passing the cone beam 23 through the beam-passable region, to achieve the purpose of conformal treatment. Of course, the shape of the beam-passable region formed by the multi-leaf collimator can be changed in various forms, e.g. the beam-passable region may correspond to part of the tumor area, and the conformal irradiation area formed by the multi-leaf collimator is not limited to the present disclosure.

In the embodiments of the present disclosure, two types of therapeutic heads, i.e. a focused therapeutic head and a conformal therapeutic head are included.

The focused therapeutic head may perform Stereotaxic Radiosurgery (SRS) or Imaging Guide Radiation Therapy (IGRT). The conformal therapeutic head may perform 3-Dimensional Conformal Radiation Therapy (3D-CRT), or Intensity Modulated Radiation Therapy (IMRT), or Stereotactic Body Radiation Therapy (SBRT), or Imaging Guide Radiation Therapy (IGRT).

Of course, the radiotherapeutic system may include other components. For example, As shown in FIGS. 1 and 2, the radiotherapeutic system includes a base 50, a gantry 40, the therapeutic heads, and a treatment couch 60. The base 50 supports the whole radiotherapeutic system 100, and plays a role of carrying the whole radiotherapeutic system 100 and a role of fixation. The treatment couch 60 is arranged on the base 50, and is movably connected to the base 50, e.g. by screws and/or pins. The treatment couch 60 is used to support and position a patient, and can accurately deliver the patient to a specified position for treatment. The gantry 40 is arranged on the base 50, and is connected to the base 50 by a rolling support. The gantry 40 rotates around an axial line by means of, e.g. gear driving.

In the radiotherapeutic system and driving control method provided with the embodiments of the present disclosure, the radiotherapeutic system includes a gantry and at least two therapeutic heads provided on the gantry. The at least two therapeutic heads include at least one focused therapeutic head and at least one conformal therapeutic head. The conformal therapeutic head can perform conformal treatment to a large area of the tumor, and the focused therapeutic head can perform a dose enhancement treatment on part of the tumor. Therefore, the radiotherapeutic system has a great advantage for some special tumor focuses where two manners of focused treatment and conformal treatment are simultaneously or separately required. In addition, with one time positioning, the conformal therapeutic head and the focused therapeutic head with multi-source in the radiotherapeutic system may implement two types of radiation therapy in combination, simultaneously or separately, therefore reducing the errors caused by multiple times of positioning, improving radiation therapy precision and speed, and improving quality and efficiency of the treatment.

The radiotherapeutic system provided by the embodiments of the present disclosure further comprises a first driving means. At least one of the therapeutic heads can be moved along a radial direction of the gantry, driven by the first driving means. Referring to FIG. 2, the radial direction of the gantry refers to the direction of the radius or diameter of the gantry. In the radiotherapeutic system provided by the present disclosure, if the therapeutic head is a conformal therapeutic head, when the therapeutic head is approaching to the axis center of gantry along the radial direction of the gantry, the beam penumbra becomes smaller, the maximum field of radiation becomes smaller, the dose rate increases, and the treatment space becomes smaller. On the contrary, if the therapeutic head is away from the axis center of the gantry along the radial direction of the gantry, the beam penumbra becomes larger, the maximum field of radiation becomes larger, the dose rate decreases, and the treatment space becomes larger.

Preferably, in the radiotherapeutic system provided in the embodiments of the present disclosure, at least the conformal therapeutic head is movable along the radial direction of the gantry, driven by the first driving means. For example, as shown in FIGS. 1 and 2, the radiotherapeutic system includes one focused therapeutic head 10 and one conformal therapeutic head 20, and preferably, the conformal therapeutic head 20 can be movable along the radial direction of the gantry. Of course, the focused therapeutic head can also be moved along the radial direction of the gantry. For example, in the case of non-rotational focusing, when the focused therapeutic head approaches the axis center of the gantry in the radial direction of the gantry, the treatment space becomes smaller. On the contrary, the treatment space becomes larger when the focused therapeutic head is away from the axis center of the gantry in the radial direction of the gantry.

Of course, each therapeutic head of the radiotherapeutic system can be moved along the radial direction of the gantry. The therapeutic space required for head radiotherapy is relatively small, and the treatment space required for the body radiotherapy is larger. For the radiotherapeutic system provided by the embodiment of the present disclosure, as the therapeutic head can move along the radial direction of the gantry, the treatment space is greater when the therapeutic head is away from the axis center of gantry. The radiotherapeutic system can also be used for body treatment, to achieve a combination of radiotherapy for head and body.

The radiotherapeutic system provided in the embodiments of the present disclosure further comprises: a second driving means, and at least one of the therapeutic heads can be moved along the axial direction of the gantry driven by the second driving means, for non-coplanar treatment. In the radiotherapeutic system, the therapeutic head can be movable along the axial direction of the gantry so that multidirectional non-coplanar treatment can be performed, to avoid localized burns to the patient during the process of radiotherapy.

In an embodiment of the present disclosure, it is preferred that at least the focused therapeutic head is movable in the axial direction of the gantry. Take the radiotherapeutic system including one focused therapeutic head 10 and one conformal therapeutic head 20 shown in FIGS. 1 and 2 as an example, preferably, the focused therapeutic head 10 can be moved along the axial direction of the gantry, to distract the patient's peripheral dose and to change the shape of the target to improve the dose distribution of the target.

Of course, each therapeutic head of the radiotherapeutic system may move along the axial direction of the gantry to vary the angle of incidence of the beam, to avoid some of the sensitive organs of interest or to improve the dose distribution.

Incidentally, in the embodiment of the present disclosure, the radiotherapeutic system may include both the first driving means and the second driving means. That is, the therapeutic head may be moved along the radial direction of the gantry and/or the axial direction of the gantry. For example, in the radiotherapeutic system as shown in FIGS. 1 and 2, the focused therapeutic head 10 and the conformal therapeutic head 20 can be moved long the radial direction of the gantry, and further can be moved long the axial direction of the gantry. In FIG. 2, the track of the focused therapeutic head 10 and the conformal therapeutic head 20 in the axial direction of the gantry are cambered. Illustratively, the two therapeutic heads are connected to the gantry through respective circular guide rails in the axial direction of the gantry, so that the therapeutic heads can be continuously translated in an axial plane of the gantry around the focal point, and the translation angle is ranged from 0 to ±47.5 degrees, to achieve non-coplanar focused treatment or conformal treatment in different incident angles, further to treat the tumor more flexibly and effectively. Specifically, the present application does not specifically limit the translation angle of the therapeutic head in the axial direction of the gantry. For example, the translation angle may be 0 to ±16 degrees.

In an embodiment of the present disclosure, the first driving means or the second driving means comprises a first driver and a movement mechanism, respectively, the movement mechanism is connected to the therapeutic head and the first driver. The first driver drives the movement mechanism to move, to further drive the movement of the therapeutic head.

Figure 3:
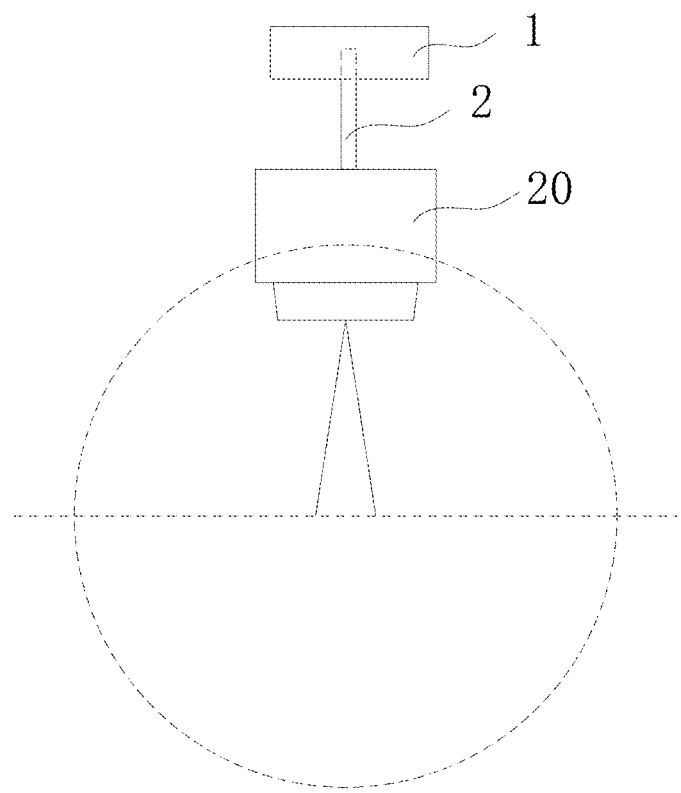
FIG. 3 is a schematic view of a conformal therapeutic head moving along a radial direction of the gantry according to an embodiment of the present disclosure.

Illustratively, taking the first driving means as an example, the movement mechanism of the first driving means comprises a lead screw 2, the first driver drives the lead screw 2 to rotate or move along a straight line, for further driving the therapeutic head to move. Illustratively, as shown in FIG. 3, the radiotherapeutic system includes a first driver 1. Taking the lead screw 2 being rotated driven by the first driver 1 as an example, the first driver 1 may include a screw hole, the lead screw 2 may include screw threads, and the lead screw 2 can be connected to the first driver 1 by screw. An end of the lead screw 2 is connected to the conformal therapeutic head 20. As such, when the first driver 1 drives the lead screw 2 to rotate, the conformal therapeutic head 20 can be driven to move along the radial direction of the gantry. Of course, for the purposes of illustration only, the therapeutic head may also be fixed with the lead screw 2, and the driver drives the lead screw 2 to perform a linear movement, so that the lead screw 2 drives the therapeutic head to move along the radial direction of the gantry.

In the above, the first driving means is illustrated as an example. However, it is understood that the second driving means may realize the axial movement of the therapeutic head in the gantry in the same or similar manner.

Figure 4:
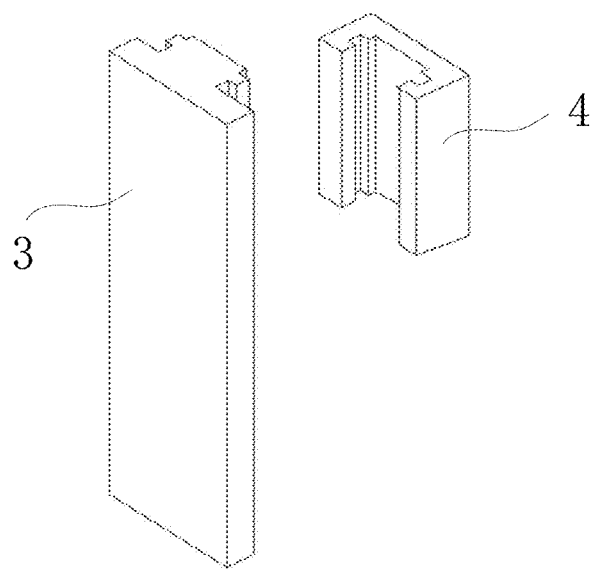
FIG. 4 is a schematic view of a guide rail and a slider according to an embodiment of the present disclosure.

Further, as shown in FIG. 4, the first driving means further comprises a guide rail 3 and a slider 4 respectively connected to the gantry 40 and the therapeutic head, and the therapeutic head is movable along the guide rail 3. In this embodiment, the guide rail 3 is connected to the gantry 40, and the slider 4 is connected to the conformal therapeutic head 20. Referring FIG. 4, the slider 4 includes a groove, and the guide rail 3 includes a protrusion engaged with the groove of the slider 4 (i.e., the protrusion of the groove resists the surface of the slider), so that the slider 4 is moved along the guide rail 3. Of course, it can also be the guide rail 3 includes the groove and the slider 4 includes the protrusion, so that the slider 4 moves along the guide rail 3.

With the movement of slider along the guide rail, the therapeutic head moves along the path of the guide rail, to prevent the therapeutic head from deviating in the radial direction of the gantry.

In the radiotherapeutic system provided by another embodiment of the present disclosure, the guide rail includes one groove or two grooves disposed on both sides thereof. That is, the concrete realization of the movement of the guide rail and the slider in the present disclosure is not particularly limited, and FIG. 4 is only shown as an illustration.

Referring to FIGS. 3 and 4, one guide rail and one slider may be fixedly attached to both sides of the therapeutic head, respectively. Of course, it is also possible to fix one or more guide rails and sliders on one side or four sides of the therapeutic head, to limit the movement path of the therapeutic head in the radial direction of the gantry, and to prevent the movement direction of the therapeutic head from deflecting.

Figure 5:
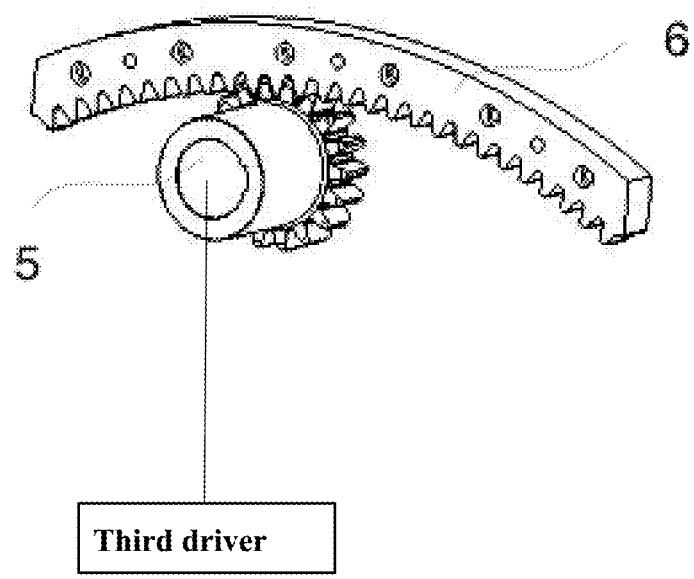
FIG. 5 is a schematic view of a gear and a gear ring according to an embodiment of the present disclosure.

Illustratively, as shown in FIG. 5, the movement mechanism of the second driving means includes a gear 5 and a gear ring 6, which are meshed with each other. The gear ring 6 is connected to the therapeutic head, and the first driver drives the gear 5 to rotate. The gear ring 6 further drives the therapeutic head to move since the gear 5 is engaged with the gear ring 6. The gear ring 6 is arc-shaped as illustrated in FIG. 5, as such, the therapeutic head with reference of FIG. 2 can be moved along the axial direction of the gantry in arc-shaped path. It is noted that the gear ring 6 may shaped as an arc with an outer circle center away from the center of the gantry, or may be a straight gear ring. The embodiment of the present disclosure is not limited to the above shape of the ring gear, what shown in FIG. 5 only is described as illustration.

Further, the second driving means further comprises another guide rail and slider which are respectively connected to the gantry and the therapeutic head, and the therapeutic head moves along the guide rail. The guide rail and the slider are used to limit the movement path of the therapeutic head in the axial direction of the gantry, so as to avoid the deviation of its movement direction. Here, as described with reference to FIG. 5, if the gear ring is arc-shaped, the guide rail would generally be arc-shaped. The specific structure of the guide rail and the slider is described with reference to FIG. 4, and will not be described in detail herein.

The radiotherapeutic system of the embodiment of the present disclosure, further comprises a third driving means which drives the therapeutic head to rotate across multiple planes or gimbally, to increase the incidence angles of the radiation beam and realize radiotherapy at more angles.

For example, the third driving means may drive the therapeutic head to rotate two planes perpendicular to each other. Or, the third driving means is connected to the therapeutic head by a gimbal so that the therapeutic head can be rotated in 360 degrees.

The radiotherapeutic system disclosed in embodiments of the present disclosure, further includes a rotation driving means (not shown). According to FIGS. 1 and 2, the gantry 40 can rotate 360 degrees continuously around the axis of the gantry 40, driven by the rotation driving means.

The gantry rotates 360 degrees around its axis, that is, the gantry can continuously rotate around the axis in the same direction. The gantry rotates about its axis reciprocally, that is, the gantry can be rotated about the axis to rotate back and forth at a certain angle. For example, the gantry rotates 270 degrees clockwise about the axis and then rotates 270 degrees counterclockwise, and so forth. Of course, the rotation degree of the gantry about the axis is not specifically limited, and the above is only an example.

As shown in FIGS. 1 and 2, the two therapeutic heads are arranged on both sides of the gantry axis, and the therapeutic heads are driven to continuously or reciprocally rotate 360 degrees around the axis line (i.e. the gyration center) of the gantry. In addition, regarding the position of the two therapeutic heads, an included angle between the focused therapeutic head 10 and the conformal therapeutic head 20 to the axis is continuously adjustable between 30 degrees and 180 degrees. Illustratively, the included angle is 90 degrees. Since the therapeutic heads can make a continuous incident angle change of maximum ±47.5 degrees and a central rotation of 360-degree around the axis, a treatment incident angle of the system may exceed $2\pi$.

Figure 6:
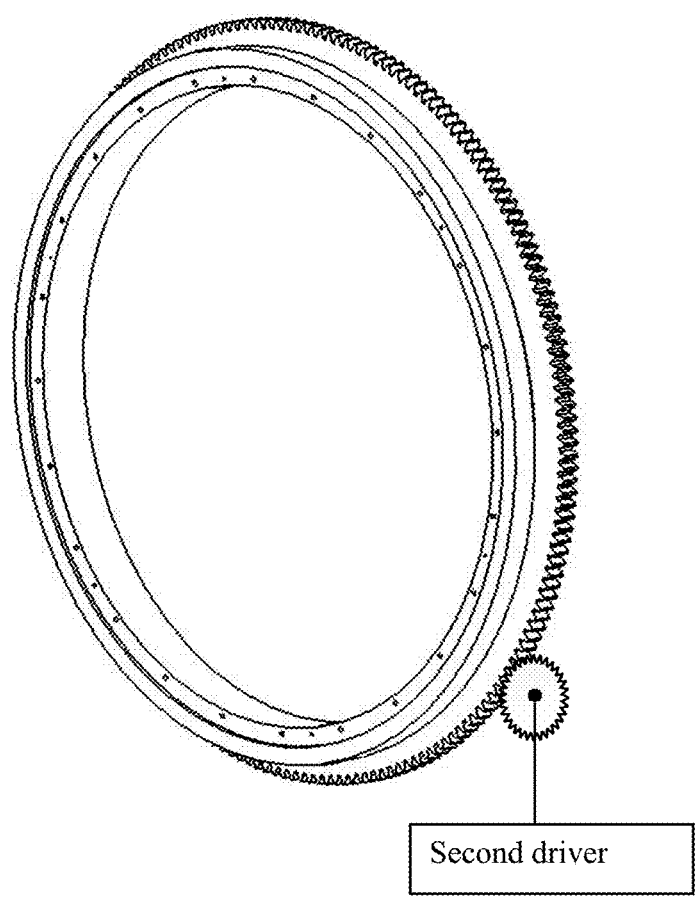
FIG. 6 is a schematic view of an outer gear ring according to an embodiment of the present disclosure.

As shown in FIG. 6, in the present embodiment, the rotation driving means includes a second driver, a drive gear, and an outer gear ring disposed on one side of the gantry. The drive gear is geared/meshed/engaged with the outer gear ring, and the second driver drives the drive gear to rotate, thereby driving the outer gear ring to rotate.

Specifically, the rotation driving means is used to drive the gantry to rotate 360 degrees continuously or reciprocally, and may include an outer gear ring 7 disposed on one side of the gantry as shown in FIG. 6. The drive gear is engaged with the outer gear ring 7, and the second driver drives the drive gear to rotate, thereby driving the outer gear ring 7 to move. The outer gear ring is connected to the gantry, so that the gantry rotates with the outer gear ring as reference with FIG. 5.

The radiotherapeutic system disclosed in embodiments of the present disclosure, wherein the focused therapeutic head with multi-source comprises a plurality of radioactive sources and a collimator, the collimator is provided with a plurality of groups of apertures in different sizes. The radiotherapeutic system further comprises a fourth driving means, configured to drive the collimator to move so that the radiation beams emitted by the radioactive source pass through the different apertures.

For example, the focused therapeutic head comprises six radioactive sources, and the collimator is provided with four groups of different sized apertures each comprising six identical collimating apertures. For example, the four groups of different sized apertures could be 4 mm, 8 mm, 12 mm and 16 mm, respectively. As such, the sizes of the radiation beams can be adjusted by moving the collimator so that the different apertures are respectively aligned with the radioactive source so as to realize the treatment of different sized radiation fields or targets. Of course, the movement of the collimator is not limited to translation, rotation or the like according to the shape of the collimator.

Of course, the collimator may also include a movable collimator and a pre-collimator. In the embodiment of the present disclosure, the radioactive sources adopt cobalt-60, to generate gamma rays. The gamma rays generated by the cobalt-60 pass through the pre-collimator and the movable collimator, and are focused on the focal point. As such, a focused field, namely, a high-dose region for therapy, is formed. The movable collimator is provided with a plurality of apertures in different size. The movement of the movable collimator is performed to switch the apertures, so as to change a size and a shape of the focused field. As such, the focused therapeutic head 10 can be used to implement accurate therapy with a small field size and a high dose.

The radiotherapeutic system disclosed according to one embodiment of the present disclosure, further comprises a fifth driving means for driving the radioactive source to move to realize turning on/off the source. Of course, it is possible to move the radioactive sources so that the radioactive source is aligned or misaligned with the apertures of the collimator, thereby switching on/off the source to implement the initiation or interruption of the treatment. It should be noted that, in some other radiotherapeutic systems, switching on/off the sources can also be realized by directly aligning or staggering the positions of the radioactive sources and a plurality of collimators. The embodiments of the present disclosure are exemplified only.

The radiotherapeutic system according to one embodiment of the present disclosure, wherein the conformal therapeutic head comprises a radioactive source and a multi-leaf collimator. The radiotherapeutic system further comprises a sixth driving means configured to switch on/off the radioactive source of the conformal therapeutic head, or control radioactive source of the conformal therapeutic head to emit radiation beams and further control the intensity of the radiation beams. The radiotherapeutic system further comprises a seventh driving means for driving the movement of the multi-leaf collimator, to form radiation field in different size and shape.

Illustratively, the conformal therapeutic head comprises a radioactive source, a pre-collimator, and a multi-leaf collimator. In the embodiment of the present disclosure, the radioactive source may be a single cobalt source or an X ray generator having an intensity greater than 4 mV. The radioactive source cooperates with the multi-leaf collimator to implement different field shapes on a treatment plane, so as to implement three-dimensional adaptive intensity modulated irradiation. The multi-leaf collimator is implemented with generally used technology, and details will not be described in the embodiment of the present disclosure.

For example, if the radioactive source of the conformal therapeutic head is an isotope radioactive source such as cobalt-60, the sixth drive means is used to switch on/off the radioactive source of the conformal therapeutic head. For example, the radioactive source is switched off by misaligning the radioactive source and the collimating apertures. If the radioactive source of the conformal therapeutic head is an accelerator device, the sixth drive means is used to control the accelerator device to emit radiation beams and further control the intensity of the radiation beams.

The multi-leaf collimator can form an irradiation field similar to shape of the tumor by the movement of the blade/leaf, so that the radiation beams from the radioactive source pass through the irradiation field and only irradiate the tumor, reducing the damage to the other important tissues surround the tumor.

The radiotherapeutic system according to an embodiment of the present disclosure, further comprises at least one group of image guided system (IGS) and an eighth driving means for driving the image guided system to collect images of the patient. Referring to FIGS. 1 and 2, take the radiotherapy system including two sets of image guided system as an example. One or two sets of stereo imaging apparatuses (i.e. X-ray generator and image detection and acquisition system) are assembled on the rotatable gantry 40 through focusing to the same focal point. Accordingly, the one or two sets of X-ray imaging apparatuses are configured to perform real-time detection of a body position and a focus space position of a patient. Space position compensation is performed for the treatment couch and the therapeutic heads according to a detection result, so as to ensure high-precision orientation during treatment and implement accurate radiation therapy. When two sets of X-ray imaging apparatuses are adopted, an included angle of two sets of imaging apparatuses is in a range of 20 degrees to 160 degrees.

For example, one set of image guided system includes a ray generator and an image detector.

The eighth driving means is configured for driving the ray generator to emit imaging beams, and configured for driving the image detector to form images of the patient according to the received imaging beams.

Specifically, the specific structure of the ray generator and the image detector can be referred to the prior art, and the embodiments of the present disclosure will not be described in detail. It should be noted that the driving approach disclosed above will be combined with other movement, including the movements of the gantry, the therapeutic heads, to complete a dynamic treatment process.

The radiotherapeutic system according to one embodiment of the present disclosure, wherein one side of the gantry is provided with a conductive slip ring connected to at least one of the first driving means, the second driving means, the third driving means, the fourth driving means, the fifth driving means, the sixth driving means, the seventh driving means, the eighth driving means, and the rotation driving means, for outputting a control signal thereto. That is, the control signal is outputted to the driving means(s) through the conductive slip ring, thereby controlling the radiotherapeutic system to realize the radiotherapy.

In general, the first driving means, the second driving means, the third driving means, the fourth driving means, the fifth driving means, the sixth driving means, the seventh driving means, the eighth driving means, or the rotation driving means may be both electrically connected to the conductive slip ring, to receive the control signal of the conductive slip ring. Of course, some of these driving means may also complete the signal transmission by other ways.

In the following, the present disclosure provides a driving control method corresponding to the above-described radiotherapeutic system.

The driving control method of the radiotherapeutic system provided by the embodiments of the present disclosure includes a controller, a gantry, a rotation driving means, and at least two therapeutic heads provided on the gantry. The at least two therapeutic heads include at least one focused therapeutic head with multi-source and at least one conformal intensity modulated therapeutic head. The driving control method comprises: sending a first driving control signal to the rotation driving means by the controller, and receiving the first driving control signal and drives the gantry to continuously or reciprocally rotate around the axis of the gantry by 360 degrees by the rotation driving means.

As an example, the radiotherapeutic system provided with reference to an embodiment of the present disclosure includes a second driver, a drive gear, and a collar disposed on one side of the gantry provided with a gear. The drive gear is meshed with the gear of the collar, and the second drive is used to drive the drive gear to rotate thereby driving the collar to rotate. The controller may specifically transmit the first driving control signal to the second driver. After receiving the first driving control signal, the second driver drives the drive gear to rotate so that the collar rotates the gantry circumferentially through the engagement of the gear. Moreover, the controller may send the first driving control signal to the second driver via a slip ring.

The radiotherapeutic system provided with reference to the driving control method of the present disclosure, further includes the first driving means, and the method further comprises: sending a second driving control signal to the first driving means by the controller, and receiving the second driving control signal and driving the therapeutic head to move along the radial direction of the gantry by the first driving means.

Illustratively, with reference to the radiotherapeutic system of an embodiment of the present disclosure, the first driving means comprises the first driver and the movement mechanism, the first driver drives the movement mechanism to move, to further drive the movement of the therapeutic head. As such, the controller may in particular send the second driving control signal to the first driver, which upon receipt of the second driving control signal drives the movement mechanism to move, such that the therapeutic head moves along the radial direction of the gantry driven by the movement mechanism. Referring to FIG. 3, the first driver 1 may drive the lead screw 2 to rotate, so that the lead screw 2 moves the conformal therapeutic head 20 along the radial direction of the gantry.

The radiotherapeutic system according to the driving control method provided with the embodiments of the present disclosure further comprises a second driving means, and the driving control method further comprises: sending a third driving control signal to the second driving means by the controller, and receiving the third driving control signal and driving the therapeutic head to move along the axial direction of the gantry by the second driving means.

Illustratively, with reference to the radiotherapeutic system of an embodiment of the present disclosure, the second driving means comprises a third driver and the movement mechanism, the third driver drives the movement mechanism to move the therapeutic head. As such, the controller may in particular send the third driving control signal to the third driver, which upon receipt of the third driving control signal drives the movement mechanism to move, such that the therapeutic head moves along the radial direction of the gantry driven by the movement mechanism. Referring to FIG. 5, the third driver may drive the gear 5 to rotate, and the gear 5 is meshed with the gear ring 6. The gear ring 6 drives the therapeutic head to move along the axial direction of the gantry.

The radiotherapeutic system according to the driving control method provided with the embodiments of the present disclosure further comprises a third driving means, and the driving control method further comprises: sending a fourth driving control signal to the third driving means by the controller, and receiving the fourth driving control signal and driving the therapeutic head to rotate across multiple planes or gimbally by the third driving means. In this embodiment, the third driving means drives the therapeutic head to rotate gimbally, to achieve a rotation in multiple angles for the therapeutic head.

The driving control method provided by the embodiments of the disclosure comprises a plurality of radioactive sources and a collimator provided with a plurality of groups of apertures in different sizes. And the driving control method further comprises: driving the collimator to move by a fourth driving means, so that the radiation beams emitted by the source can emit through different apertures.

The driving control method according to an embodiment of the present disclosure further comprises: driving the radioactive source to move to realize turning on/off the source by a fifth driving means.

In the driving control method according to an embodiment of the present disclosure, the conformal therapeutic head comprises a radioactive source and a multi-leaf collimator. The driving control method further includes: controlling switching on/off of the radioactive source of the conformal therapeutic head, or controlling the radioactive source of the conformal therapeutic head to emit radiation beams and controlling the radiation intensity thereof by a sixth driving means, and driving the multi-leaf collimator to move to form irradiation fields in different sizes and shapes by a seventh driving means.

In the driving control method according to an embodiment of the present disclosure, the radiotherapeutic system further includes at least one set of image guided system, and the driving control method further comprises: driving the image guided system to capture images of the patient by the eighth drive means. Referring to FIGS. 1 and 2, the radiotherapy system includes two sets of image guided system, as an example.

Illustratively, the image guided system comprises a radiation generator and an image detector. The eighth driving means drives the radiation generator to emit imaging beams, and drives the image detector to form the images of the patient in response to the received radiation beams.

Specifically, the specific structure of the radiation generator and the image detector can be referred to the prior art, and the embodiments of the present disclosure will not be described in detail. It should be noted that the above driving means will be combined with other movement, including the movement of the gantry, the therapeutic head to complete a dynamic treatment process.

According to the driving control method of the present disclosure, the controller includes: local controller and/or remote controller. The local controller is generally located in a control room of the radiotherapeutic system accessories, the operator in the control room controls the radiotherapeutic system/system to work through the local controller, to complete the radiotherapy process. The remote controller may be a remote controller or a cloud controller that controls the operation of the radiotherapeutic apparatus by performing a communication connection with the radiotherapeutic system to complete the course of the radiotherapy. For example, it can be the local controller or the remote controller to send the driving signal to the first driving means, the second driving means, the fourth driving means, the fifth driving means, the sixth driving means, the seventh driving means, the eighth driving means, and the rotation driving means.

The controller included the local controller and/or remote controller, may include only the local controller, or only the remote controller, or include the local controller and further the remote controller.

According to the driving control method of the present disclosure, if the controller further includes the remote controller, the radiotherapeutic system transmits a current device parameters thereof to the remote controller, and the remote controller determines the performance index or status of the radiotherapeutic system, based on the received device parameters of the radiotherapeutic system.

Illustratively, the device parameters of the radiotherapeutic system include at least the operating state parameters, the performance parameters, the safety control parameters, etc. For example, the radiotherapy system is located in Beijing, and the remote controller is located in Shenzhen, and the radiotherapy system sends the current performance parameters of the radiotherapeutic system to the remote controller located in Shenzhen, then the equipment maintenance person in Shenzhen can learn of the operation status of the equipment in Beijing, and timely determine the performance of the radiotherapeutic system. For example, if it is found that the accuracy of the device is reduced, the person concerned may be notified to perform maintenance of the equipment.

Further, the remote controller sends the performance index or status of the radiotherapeutic system to the local controller, and the local controller adjusts the parameters of the radiotherapeutic system according to the performance index or status of the radiotherapeutic system. That is, the local control system can further confirm the operation state of the radiotherapeutic system according to the received parameters of the radiotherapeutic system, and correct and maintain the radiotherapeutic system.

Alternatively, the remote controller adjusts the parameters of the radiotherapeutic system according to the performance index or status of the radiotherapeutic system, and sends the parameters to the local controller. That is, the remote controller directly corrects and maintains the parameters of the radiotherapeutic system.

The steps of the method or algorithm described in the present disclosure may be implemented in hardware, or in a manner that the processor executes software instructions. The software instructions may be composed of corresponding software modules which may be stored in a random access memory (RAM), a flash memory, a read only memory (ROM), an erasable programmable read only memory (EPROM), electrically programmable read only memory (EEPROM), registers, hard disk, removable hard disk, CD-ROM, or any other form of storage medium known in the art. An exemplary storage medium is coupled to the processor such that the processor can read information from and write information to the storage medium. Of course, the storage medium can also be an integral part of the processor. The processor and the storage medium may be located in ASIC. In addition, the ASIC may be located in a core network interface device. Of course, the processor and the storage medium may also exist as discrete components in the core network interface device.

It should be appreciated by those skilled in the art that the functions described herein may be implemented in hardware, software, firmware, or any combination thereof, in one or more of the above-described examples. When implemented using software, these functions may be stored on a computer-readable medium or transmitted as one or more instructions or code on a computer-readable medium. The computer-readable medium includes a computer storage medium and a communication medium, wherein the communication medium includes any medium that facilitates transfer of a computer program from one place to another. The storage medium may be any available medium that can be accessed by a general purpose or special purpose computer.

It is to be understood that the foregoing is intended only as a specific embodiment of the disclosure and is not intended to limit the scope of the disclosure. The scope of protection of the present disclosure is to be understood to be within the scope of the present disclosure as defined by the equivalents thereof or equivalents thereof or to any other related art, either directly or indirectly, by the use of the present specification and drawings.

I claim:

1. A radiotherapeutic system, comprising a gantry and at least two radiotherapeutic heads disposed to the gantry, wherein the at least two radiotherapeutic heads comprise at least one focused radiotherapeutic head with multi-source and at least one conformal and intensity-modulated radiotherapeutic head, the focused radiotherapeutic head with multi-source comprises a plurality of radioactive sources and a collimator, and the conformal and intensity-modulated radiotherapeutic head comprises a radioactive source and a multi-leaf collimator.

2. The radiotherapeutic system of claim 1, further comprising a first driving means configured for driving at least one of the therapeutic heads to moved along a radial direction of the gantry.

3. The radiotherapeutic system of claim 2, further comprising a second driving means configured for driving at least one of the therapeutic heads to move along the axial direction of the gantry, to perform non-coplanar treatment.

4. The radiotherapeutic system of claim 3, wherein the first driving means or the second driving means comprises a first driver and a movement mechanism, the movement mechanism is connected to the therapeutic head and the first driver, the first driver drives the movement mechanism to move to further drive the movement of the therapeutic head.

5. The radiotherapeutic system of claim 4, wherein the movement mechanism comprises a gear and a gear ring which are meshed with each other, the gear ring is connected to the therapeutic head, and the first driver drives the gear to rotate to further drive the therapeutic head to move.

6. The radiotherapeutic system of claim 3, wherein the first or second driving means further comprises a guide rail and a slider which are respectively connected to the gantry and the therapeutic head, and the therapeutic head moves along the guide rail.

7. The radiotherapeutic system of claim 3, further comprising a third driving means configured for driving the therapeutic head to rotate across multiple planes or gimbally.

8. The radiotherapeutic system of claim 7, further comprising a rotation driving means configured for driving the gantry to rotate 360 degrees around the axis of the gantry continuously or reciprocally, and the rotation driving means comprises: a second driver, a drive gear, and an outer gear ring disposed on one side of the gantry, the drive gear is geared with the outer gear ring, and the second driver is configured for driving the drive gear to rotate, thereby driving the outer gear ring to rotate.

9. The radiotherapeutic system of claim 8, wherein the collimator is provided with a plurality of groups of apertures in different sizes; and the radiotherapeutic system further comprises a fourth driving means configured to drive the collimator to move so that the radiation beams emitted by the radioactive source pass through the different apertures.

10. The radiotherapeutic system of claim 9, wherein the radiotherapeutic system further comprises a sixth driving means configured for controlling the radioactive source of the conformal and intensity-modulated therapeutic head to switch on/off or emit radiation beams and further controlling the radiation intensity thereof; and the radiotherapeutic system further comprises a seventh driving means configured for driving the multi-leaf collimator to move to form irradiation fields in different sizes and shapes.

11. The radiotherapeutic system of claim 10, further comprising at least one set of image guided system and an eighth drive means configured for driving the image guided system to capture images of the patient.

12. The radiotherapeutic system of claim 11, wherein one side of the gantry is provided with a conductive slip ring connected to at least one of the first driving means, the second driving means, the third driving means, the fourth driving means, the sixth driving means, the seventh driving means, the eighth driving means, and the rotation driving means, for outputting a control signal thereto.

13. A driving control method used in a radiotherapeutic system, wherein the radiotherapeutic system comprises a controller, a gantry, a rotation driving means, and at least two therapeutic heads provided on the gantry, and the at least two therapeutic comprises at least one focused therapeutic head with multi-source and at least one conformal and intensity-modulated therapeutic head, and wherein the driving control method comprises the step of:

sending a first driving control signal to the rotation driving means by the controller; and receiving, by the rotation driving means, the first driving control signal and driving the gantry to continuously or reciprocally rotate around the axis of the gantry by 360 degrees.

14. The driving control method of claim 13, wherein the radiotherapeutic system further comprises a first driving means, and the method further comprises: sending a second driving control signal to the first driving means by the controller, and receiving the second driving control signal and driving the therapeutic head to move along the radial direction of the gantry by the first driving means.

15. The driving control method of claim 13, wherein the radiotherapeutic system further comprises a second driving means, and the driving control method further comprises:

sending a third driving control signal to the second driving means by the controller, and receiving the third driving control signal and driving the therapeutic head to move along the axial direction of the gantry by the second driving means.

16. The driving control method of claim 13, wherein the radiotherapeutic system further comprises a third driving means, and the driving control method further comprises:

sending a fourth driving control signal to the third driving means by the controller, and receiving the fourth driving control signal and driving the therapeutic head to rotate across multiple planes or gimbally by the third driving means.

17. The driving control method of claim 13, wherein the focused therapeutic head with multi-source comprises a plurality of radioactive sources and a collimator, the collimator is provided with a plurality of groups of apertures in different sizes; and the driving control method further comprises: driving the collimator to move by a fourth driving means so that the radiation beams emitted by the radioactive source pass through the different apertures.

18. The driving control method of claim 13, wherein the conformal and intensity-modulated therapeutic head comprises a radioactive source and a multi-leaf collimator;

the driving control method further comprises: controlling the radioactive source of the conformal and intensity-modulated therapeutic head to switch on/off or emit radiation beams and further controlling the radiation intensity thereof by a sixth driving means; and driving the multi-leaf collimator to move to form irradiation fields in different sizes and shapes by a seventh driving means.

19. The driving control method of claim 13, wherein the radiotherapeutic system further comprises at least one set of image guided system comprising a radiation generator and an image detector; and the driving control method further comprises:

driving the radiation generator to emit imaging beams and driving the image detector to form the images of the patient in response to the received radiation beams by an eighth drive means.

20. The driving control method of claim 13, wherein the controller comprises a local controller and/or a remote controller; and when the controller further comprises the remote controller, the radiotherapeutic system transmits a current device parameters thereof to the remote controller, wherein the device parameters of the radiotherapeutic system comprises at least the operating state parameters, the performance parameters, the safety control parameters; and the remote controller determines the performance index or status of the radiotherapeutic system, based on the received device parameters of the radiotherapeutic system; or the remote controller sends the performance index or status of the radiotherapeutic system to the local controller, and the local controller adjusts the parameters of the radiotherapeutic system according to the performance index or status of the radiotherapeutic system; or the remote controller adjusts the parameters of the radiotherapeutic system according to the performance index or status of the radiotherapeutic system, and sends the parameters to the local controller.

* * * * *